United States Patent [19]

Rudolph

[11] Plant 4,246

[45] May 2, 1978

[54] PEONY PLANT NAMED AMERICA

[75] Inventor: Nathan H. Rudolph, Aurora, Ill.

[73] Assignee: Klehm Boys Partnership, Arlington Heights, Ill.

[21] Appl. No.: 795,165

[22] Filed: May 9, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new cultivar of *Paeonia lobata* distinguished by its profuse production of large, scarlet red flowers held high above an abundant display of mint green foliage carried on large, tall canes, the imbricated flower petals forming a fiery red bowl surrounding a central mass of bright yellow stamens to present a spectacular color effect. This new peony plant has an abnormally early spring blooming habit and its growth is vigorous and rapid with above average strength and sturdiness.

1 Drawing Figure

BACKGROUND OF THE NEW PLANT

My new peony plant originated as a seedling of Burma Ruby (unpatented) and an unknown pollen parent and was discovered by me in 1960 at my breeding grounds in Aurora, Ill., where I have been exploring the gene pool of its truly outstanding seed parent since 1953. The fine and unusual appearance of this new plant prompted me to propagate it by root division to test its characteristics of growth and flower production and continued propagation through successive generations, by root division, at my Aurora, Ill., gardens has demonstrated conclusively that the novel features of this plant hold true from generation to generation and are firmly fixed.

DESCRIPTION OF THE DRAWING

My new variety of peony is illustrated by the accompanying photographic drawing which shows blossoms of the new plant in full color, the colors shown being as nearly true as it is reasonably possible to obtain by conventional procedure for photographic color reproduction.

DESCRIPTION OF THE NEW PLANT

The following is a detailed description of this new peony cultivar with color specifications according to the R.H.S. Colour Chart published by the Royal Horticultural Society of London, England, the observations having been made in 1976 at Aurora, Ill.

THE PLANT

Origin: Seedling.
Parentage:
*Seed parent.*—Burma Ruby (unpatented).
*Pollen parent.*—Unknown.
Classification:
*Paeonia lobata* hybrid.
Form: Bush of round shape.
Height: 36 to 38 inches.
Growth: Vigorous and upright with above average sturdiness and strength.
*Growth rate.*—Rapid.
*Cane size.*—1¼ to 1½ inches at the base.
Foliage: Quantity — abundant with numerous leaves.
*Shape of leaves.*—Elliptically acute with smooth margins.

*Appearance.*—Smooth and glossy.
*Color.*—Upper side — Forest Green RHS 135A. Under side — Almond Green RHS 135B.

THE BUD

Form: Round.
Size: Medium.
*Diameter.*—1¼ inches.
*Depth.*—1¼ inches.
Rate of opening: Average.
Color:
*When sepals first divide.*—RHS 43A.
*When petals begin to unfurl.*—RHS 44A.
Sepals: Hooded over the bud.
*Color.*—Inside — Limpid Green RHS 135D. Outside — Medium Green RHS 135C.
Calyx: Shape — polysepalous.
*Size.*—Broad.
*Aspect.*—Smooth.
*Splitting.*—The calyx does not split.

THE FLOWER

Blooming habit: Annually and profusely.
Blooming period: Abnormally early in spring.
Borne: Singly.
Size: Large.
Shape: Cup shaped with high center when bloom first opens becoming saucer shaped as bloom matures.
Petalage: Number — 12 to 14 petals.
*Arrangement.*—Imbricated.
*Shape.*—Round-spatulate
*Margin type.*—Creped, occasionally notched.
*Color.*—Petal body, upper side and reverse, Scarlet Red RHS 44A-B, with occasional washed white areas at petal end margins.
*Texture.*—Soft.
*Appearance.*—Satiny.
Petaloids: None.
Persistence: Petals drop freely at end of term.
Fragrance: Slight peony.
Disease resistance: This variety appears to resist leaf blotch and botrytis in areas where these diseases are present.
Lasting quality:
*On plant.*—Average, 7 to 9 days.
*As cut flower.*—Average.

REPRODUCTIVE ORGANS

Stamens:

*Arrangement.* — Centralized mass.

*Number.*—Numerous.

*Filaments.*—Length — ½ to ⅝ inch. Color: Yellow.

*Pollen.*—Color — Aureolin RHS 12A.

Pistils: Number — 2 or 3.

*Styles.*—¾ to 1 inch long.

*Stigmas.*—Color — white.

Ovaries: Plump, but hollow.

My new variety of peony plant is particularly characterized by its abnormally early spring blooming period and its almost indescribable fiery red blossoms which are carried on tall, very strong stems above abundant and most attractive foliage. This variety has a vigorous and rapid growing habit and is a strong, healthy plant with large flowers that open with a unique cupped shape, somewhat like that of a Darwin tulip, to provide a striking and unusual color contrast with its mint green foliage.

I claim:

1. A new and distinct peony cultivar substantially as herein shown and described, characterized by its large, fiery red flowers carried on strong, tall stems above an abundant growth of mint green foliage, by its vigorous, strong and healthy growth and by its very early spring flowering habit.

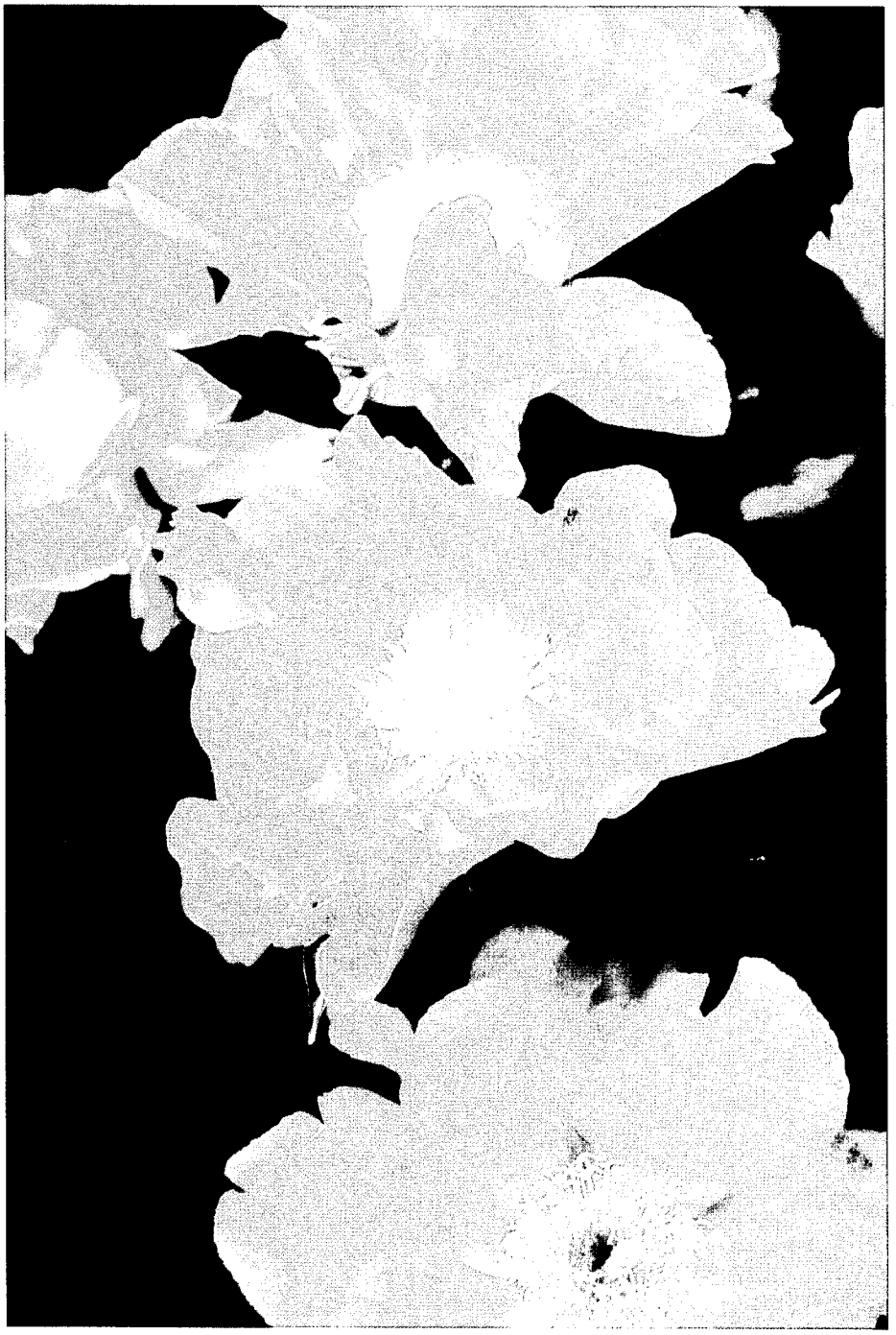

* * * * *